United States Patent [19]
Lambert, Jr.

[11] Patent Number: 5,888,973
[45] Date of Patent: *Mar. 30, 1999

[54] ANTI-CHLAMYDIAL USES OF BPI PROTEIN PRODUCTS

[75] Inventor: Lewis H. Lambert, Jr., Fremont, Calif.

[73] Assignee: XOMA Corporation, Berkeley, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 694,843

[22] Filed: Aug. 9, 1996

[51] Int. Cl.$^6$ .............................. A61K 38/00; C07K 17/00
[52] U.S. Cl. .............................. 514/12; 514/21; 530/324; 530/350
[58] Field of Search ........................ 514/12, 21; 530/324, 530/350

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott et al. | 514/12 |
| 5,198,541 | 3/1993 | Elsbach et al. | 435/69.1 |
| 5,234,912 | 8/1993 | Marra et al. | 514/12 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |
| 5,420,019 | 5/1995 | Theofan et al. | 435/69.1 |
| 5,439,807 | 8/1995 | Grinna et al. | 435/69.1 |
| 5,447,913 | 9/1995 | Ammons et al. | 514/12 |
| 5,466,580 | 11/1995 | White et al. | 435/7.1 |
| 5,466,581 | 11/1995 | White et al. | 435/7.32 |
| 5,484,705 | 1/1996 | White et al. | 435/7.32 |
| 5,488,034 | 1/1996 | McGregor et al. | 514/12 |
| 5,494,896 | 2/1996 | Hansbrough | 514/12 |
| 5,523,288 | 6/1996 | Cohen et al. | 514/12 |
| 5,532,216 | 7/1996 | Espevik et al. | 514/12 |
| 5,576,292 | 11/1996 | Elsbach et al. | 514/12 |
| 5,578,568 | 11/1996 | Ammons et al. | 514/12 |
| 5,578,572 | 11/1996 | Horwitz et al. | 514/12 |
| 5,627,153 | 5/1997 | Little et al. | 514/12 |
| 5,639,727 | 6/1997 | Little et al. | 514/12 |
| 5,641,874 | 6/1997 | Elsbach et al. | 536/23.1 |
| 5,643,570 | 7/1997 | Theofan et al. | 424/134.1 |
| 5,643,875 | 7/1997 | Friedman et al. | 514/12 |
| 5,646,114 | 7/1997 | Lambert | 514/12 |
| 5,652,332 | 7/1997 | Little | 530/324 |
| 5,674,834 | 10/1997 | Theofan et al. | 514/12 |
| 5,696,090 | 12/1997 | McGregor et al. | 514/12 |
| 5,703,038 | 12/1997 | Ammons et al. | 514/2 |
| 5,733,872 | 3/1998 | Little | 514/12 |

FOREIGN PATENT DOCUMENTS

| | | |
|---|---|---|
| WO 89/01486 | 2/1989 | WIPO . |
| Wo 90/09183 | 8/1990 | WIPO . |
| WO 92/03535 | 3/1992 | WIPO . |
| WO 92/09621 | 6/1992 | WIPO . |
| WO 93/05797 | 4/1993 | WIPO . |
| WO 93/06228 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |
| WO 94/20532 | 9/1994 | WIPO . |
| Wo 94/21280 | 9/1994 | WIPO . |
| WO 94/25476 | 11/1994 | WIPO . |
| WO 95/01428 | 1/1995 | WIPO . |
| WO 95/02414 | 1/1995 | WIPO . |
| Wo 95/00641 | 1/1995 | WIPO . |
| WO 95/08344 | 3/1995 | WIPO . |
| WO 95/08773 | 3/1995 | WIPO . |
| WO 95/10297 | 4/1995 | WIPO . |
| WO 95/19179 | 7/1995 | WIPO . |
| WO 95/19180 | 7/1995 | WIPO . |
| WO 95/19372 | 7/1995 | WIPO . |
| WO 95/19784 | 7/1995 | WIPO . |
| WO 95/20163 | 7/1995 | WIPO . |
| WO 95/24209 | 9/1995 | WIPO . |
| WO 96/01647 | 1/1996 | WIPO . |
| WO 96/08509 | 3/1996 | WIPO . |
| WO 96/21436 | 7/1996 | WIPO . |
| WO 96/30037 | 10/1996 | WIPO . |
| WO 97/04008 | 2/1997 | WIPO . |
| WO 97/17989 | 5/1997 | WIPO . |
| WO 97/17990 | 5/1997 | WIPO . |
| WO 97/42966 | 11/1997 | WIPO . |
| WO 97/42967 | 11/1997 | WIPO . |
| WO 97/44056 | 11/1997 | WIPO . |
| WO 98/06415 | 2/1998 | WIPO . |

OTHER PUBLICATIONS

Alexander et al., "Role of *Chlamydia trachomatis* in Perinatal Infection," *Rev. Infect. Dis.,* 5(4):713–719 (Jul.–Aug. 1983).

Becker, "The Chlamydia: Molecular Biology of Procaryotic Obligate Parasites of Eucaryocytes," *Microbiol., Rev.,* 42(2):274–306 (Jun. 1978).

Beatty et al., "Persistent Chlamydiae: from Cell Culture to a Paradigm for Chlamydial Pathogenesis," *Microbiol. Rev.,* 58(4):686–699 (Dec., 1994).

Brade et al., "Antigenic Properties of *Chlamydia trachomatis* Lipopolysaccharide," *Infect.Immun.,* 48(2):569–572 (May, 1985).

Brade et al., "Chlamydial lipopolysaccharide," *J. Endotoxin Res.,* 4(1):67–84 (1997).

Brade et al., "Chlamydial LPS: More than a Genus–Specific Antigen?," *Chlamydial Infections,* Proceedings of the 8th Int'l Symposium on Human Chlamydial Infections Jun. 19–24, 1994, Orfila et al., eds., Societa Editrice Esculapio, Bologna, Italy, pp. 247–250.

(List continued on next page.)

*Primary Examiner*—Cecilia J. Tsang
*Assistant Examiner*—Abdel A. Mohamed
*Attorney, Agent, or Firm*—Marshall, O'Toole, Gerstein, Murray & Borun

[57] ABSTRACT

The present invention relates to methods for treating chlamydial infection comprising administering to a subject suffering from a chlamydial infection a bactericidal/permeability-inducing (BPI) protein product.

13 Claims, No Drawings

OTHER PUBLICATIONS

Bowie, "Treatment of Chlamydial Infections," *Chlamydial Infections*, Proceedings of the 8th Int'l Symposium on Human Chlamydial Infections Jun. 19–24, 1994, Orfila et al., eds., Societa Editrice Esculapio, Bologna, Italy, pp. 621–630.

Campbell et al., "Detection of *Chlamydia Pneumoniae* in Atherectomy Tissue From Patients with Symptomatic Coronary Artery Disease," *Chlamydial Infections*, Proceedings of the 8th Int'l Symposium on Human Chlamydial Infections Jun. 19–24, 1994, Orfila et al., eds., Societa Editrice Esculapio, Bologna, Italy, pp. 212–215.

Chen et al., "Differences in High Affinity Binding of Heparin to Trachoma and LGV Biovars of *Chlamydia Trachomatis*," *Chlamydial Infections*, Proceedings of the 8th Int'l Symposium on Human Chlamydial Infections Jun. 19–24, 1994, Orfila et al., eds., Societa Editrice Esculapio, Bologna, Italy, pp. 387–390.

Elsbach and Weiss, "Oxygen–Independent Antimicrobial Systems of Phagocytes," *In Inflammation: Basic Principles and Clinical Correlates*, Chapter 30, Gallin et al., (Eds.), Second Edition, Raven Press, Ltd., New York, pp. 603–636 (1992).

Gaydos et al., "Growth Characteristics of *Chlamydia Pneumoniae* in Macrophages and Endothelial Cells," *Chlamydial Infections*, Proceedings of the 8th Int'l Symposium on Human Chlamydial Infections Jun. 19–24, 1994, Orfila et al., eds., Societa Editrice Esculapio, Bologna, Italy, pp. 216–219.

Elsbach et al., "Separation and Purification of a Potent Bactericidal/Permeability Increasing Protein and a Closely Associated Phospholipase $A_2$ From Rabbit Polymorphonuclear Leukocytes," *J. Biol. Chem.*, 254(21):11000–11009 (Nov. 10, 1979).

Gazzano–Santoro et al., "High–Affinity Binding of the Bactericidal/Permeability–Increasing Protein and a Recombinant Amino–Terminal Fragment to the Lipid A Region of Lipopolysaccharide," *Infect. Immun.* 60 (11):4754–4761 (Nov., 1992).

Gray et al., "Cloning of the cDNA of a Human Neutrophil Bactericidal Protein," *J. Biol. Chem.*, 264(16):9505–9509 (Jun. 5, 1989).

Grayston et al., *Chlamydial Infections*, Proceedings of the 8th Int'l Symposium on Human Chlamydial Infections Jun. 19–24, 1994, Orfila et al., eds., Societa Editrice Esculapio, Bologna, Italy, pp. 199–208.

Grayston et al., "New Knowledge of Chlamydie and the Diseases They Cause," *J. Infect. Dis.*, 132(1): 87–105 (Jul. 1975).

Hatch et al., "Identification of a Major Envelope Protein in Chlamydia spp.," *J. Bacteriol.*, 146(1):426–429 (Apr. 1981).

In't Veld et al., "Effects of the Bactericidal/Permeability–Increasing Protein of Polymorphonuclear Leukocytes on Isolated Bacterial Cytoplasmic Membrane Vesicles," *Infection and Immunity*, 56(5):1203–1208 (May, 1988).

Leinonen et al., "*Chlamydia Pneumoniae*–Specific Antibodies and Immune Complexes in German Patients with Acute Myocardial Infarction," *Chlamydial Infections*, Proceedings of the 8th Int'l Symposium on Human Chlamydial Infections Jun. 19–24, 1994, Orfila et al., eds., Societa Editrice Esculapio, Bologna, Italy, pp. 209–211.

Levy et al., "Antibacterial 15–kDa Protein Isoforms (p15s) Are Members of a Novel Family of Leukocyte Proteins," *J. Biol. Chem.*, 268(8):6058–6063 (Mar. 16, 1993).

Lycke, "Assaying Antichlamydial Drugs in Vitro," *Scand. J. Infect. Dis. Suppl.* 32 :38–41 (1982).

Mannion et al., "Separation of Sublethal and Lethal Effects of Polymorphonuclear Leukocytes on *Escherichia coli*," *J. Clin. Invest.*, 86:631–641 (Aug., 1990).

Mannion et al., "Separation of Sublethal Effects of the Bactericidal/Permeability Increasing Protein on *Escherichia coli*," *J. Clin. Invest.*, 85:853–860 (Mar., 1990).

McCormack, W.M., (Ed.), "Chlamydia Monograph," Abbott Diagnostics Educational Services, pp. 3–23, 1983.

Nurminen et al., "Chemical Characterization of *Chlamydia trachomatis* Lipopolysaccharide," *Infect. Immun.*, 48(2):573–575 (May 1985).

Nurminen et al., "The Genus–Specific Antigen of Chlamydia: Resemblance to the Lipopolysaccharide of Enteric Bacteria," *Science* 220 :1279–1281 (Jun. 17 1983).

Ooi et al., "A 25–kDa $NH_2$–Terminal Fragment Carries All the Antibacterial Activities of the Human Neutrophil 60–kDa Bactericidal/Permeability–Increasing Protein," *J. Biol. Chem.*, 262(31):14891–14894 (Nov. 5, 1987).

Ooi et al., "Endotoxin Neutralizing Properties of the 25 kD N–Terminal Fragment of the 55–60 kD Bactericidal/Permeability–Increasing Protein of Human Neutrophils," *J. Exp. Med.*, 174:649–655 (Sep., 1991).

Peeling et al., "Standardization of Antimicrobial Susceptibility Testing for *Chlamydia trachomatis*," *Chlamydial Infections*, Proceedings of the 8th Int'l Symposium on Human Chlamydial Infections Jun. 19–24, 1994, Orfila et al., eds., Societa Editrice Esculapio, Bologna, Italy, pp. 346–349.

Salari et al., "Polypeptide Composition of *Chlamydia trachomatis*," *J. General Microbiol.*, 123:197–207 (1981).

Ooi et al., "Isolation of Two Isoforms of a Novel 15–kDa Protein from Rabbit Polymorphonuclear Leukocytes That Modulate the Antibacterial Actions of Other Leukocyte Proteins," *J. Biol. Chem.*, 265:15956–15962 (Sep. 15, 1990).

Schachter and Stamm, "Chlamydia," In: *Manual of Clinical Microbiology*, American Society of Microbiology, Washington, DC, pp. 669–677 (1995).

Schachter et al., "In Vitro Activity of Ciprofloxacin against *Chlamydia trachomatis*," *Am. J. Med.*, 82 (Suppl. 4A):42–43 (Apr. 27, 1987).

Stephens, "Cell Biology of Chlamydia Infection," *Chlamydial Infections*, Proceedings of the 8th Int'l Symposium on Human Chlamydial Infections Jun. 19–24, 1994, Orfila et al., eds., Societa Editrice Esculapio, Bologna, Italy, pp. 377–386.

Walker and Dasch, "Classification and Identification of Chlamydia, Rickettsia, and Related Bacteria," pp. 665–668, 1993.

Weiss et al., "Cellular and Subcellular Localization of the Bactericidal/Permeability–Increasing Protein of Neutrophils," *Blood*, 69(2):652–659 (Feb., 1987).

Weiss et al., "Human Bactericidal/Permeability–Increasing Protein and a Recombinant $NH_2$–Terminal Fragment Cause Killing of Serum–Resistant Gram–Negative Bacteria in Whole Blood and Inhibit Tumor Necrosis Factor Release Induced by the Bacteria," *J. Clin. Invest.*, 90:1122–1130 (Sep., 1992).

Weiss et al., "Resistance of Gram–Negative Bacteria to Purified Leukocyte Proteins," *J. Clin. Invest.*, 65:619–628 (Mar., 1980).

Weiss et al., "The Role of Lipopolysaccharide in the Action of the Bactericidal/Permeability Neutrophil Protein on the Bacterial Envelope," *J. Immunol.*, 132(6):3109–3115 (Jun., 1984).

Weiss et al., Failure to Detect *Chlamydia Pneumoniae* (Cp) in Coronary Atheromas of Patients Undergoing Atherectomy," *Chlamydial Infections,* Proceedings of the 8th Int'l Symposium on Human Chlamydial Infections Jun. 19–24, 1994, Orfila et al., eds., Societa Editrice Esculapio, Bologna, Italy, pp. 220–223.

Yasin et al., "Protegrins: Structural Requirements For Activity Against *Chlamydia trachomatis,*" 96th ASM General Meeting, Session 17, p. 242, (Abstract D–3).

Yasin et al., "Susceptibility of *Chlamydia trachomatis* to Natural Peptide Antibiotics," (Abstract D–163).

Zhang et al., "Mechanism of *C. trachomatis* Attachment to Eukaryotic Host Cells," *Cell,* 69:861–869 (May 29, 1992).

5,888,973

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( i x ) FEATURE:
        ( A ) NAME/KEY: misc_feature
        ( D ) OTHER INFORMATION: "rBPI"

( x i ) SEQUENCE DESCRIPTION: SEQ ID NO:1:

```
CAGGCCTTGA  GGTTTTGGCA  GCTCTGGAGG  ATG  AGA  GAG  AAC  ATG  GCC  AGG  GGC                54
                                    Met  Arg  Glu  Asn  Met  Ala  Arg  Gly
                                    -31  -30                      -25

CCT  TGC  AAC  GCG  CCG  AGA  TGG  GTG  TCC  CTG  ATG  GTG  CTC  GTC  GCC  ATA          102
Pro  Cys  Asn  Ala  Pro  Arg  Trp  Val  Ser  Leu  Met  Val  Leu  Val  Ala  Ile
              -20                  -15                      -10

GGC  ACC  GCC  GTG  ACA  GCG  GCC  GTC  AAC  CCT  GGC  GTC  GTG  GTC  AGG  ATC          150
Gly  Thr  Ala  Val  Thr  Ala  Ala  Val  Asn  Pro  Gly  Val  Val  Val  Arg  Ile
              -5                        1                   5

TCC  CAG  AAG  GGC  CTG  GAC  TAC  GCC  AGC  CAG  CAG  GGG  ACG  GCC  GCT  CTG          198
Ser  Gln  Lys  Gly  Leu  Asp  Tyr  Ala  Ser  Gln  Gln  Gly  Thr  Ala  Ala  Leu
10                       15                  20                           25

CAG  AAG  GAG  CTG  AAG  AGG  ATC  AAG  ATT  CCT  GAC  TAC  TCA  GAC  AGC  TTT          246
Gln  Lys  Glu  Leu  Lys  Arg  Ile  Lys  Ile  Pro  Asp  Tyr  Ser  Asp  Ser  Phe
               30                            35                      40

AAG  ATC  AAG  CAT  CTT  GGG  AAG  GGG  CAT  TAT  AGC  TTC  TAC  AGC  ATG  GAC          294
Lys  Ile  Lys  His  Leu  Gly  Lys  Gly  His  Tyr  Ser  Phe  Tyr  Ser  Met  Asp
               45                      50                       55

ATC  CGT  GAA  TTC  CAG  CTT  CCC  AGT  TCC  CAG  ATA  AGC  ATG  GTG  CCC  AAT          342
Ile  Arg  Glu  Phe  Gln  Leu  Pro  Ser  Ser  Gln  Ile  Ser  Met  Val  Pro  Asn
          60                            65                  70

GTG  GGC  CTT  AAG  TTC  TCC  ATC  AGC  AAC  GCC  AAT  ATC  AAG  ATC  AGC  GGG          390
Val  Gly  Leu  Lys  Phe  Ser  Ile  Ser  Asn  Ala  Asn  Ile  Lys  Ile  Ser  Gly
     75                            80                       85

AAA  TGG  AAG  GCA  CAA  AAG  AGA  TTC  TTA  AAA  ATG  AGC  GGC  AAT  TTT  GAC          438
Lys  Trp  Lys  Ala  Gln  Lys  Arg  Phe  Leu  Lys  Met  Ser  Gly  Asn  Phe  Asp
90                       95                       100                     105

CTG  AGC  ATA  GAA  GGC  ATG  TCC  ATT  TCG  GCT  GAT  CTG  AAG  CTG  GGC  AGT          486
Leu  Ser  Ile  Glu  Gly  Met  Ser  Ile  Ser  Ala  Asp  Leu  Lys  Leu  Gly  Ser
                    110                           115                     120

AAC  CCC  ACG  TCA  GGC  AAG  CCC  ACC  ATC  ACC  TGC  TCC  AGC  TGC  AGC  AGC          534
Asn  Pro  Thr  Ser  Gly  Lys  Pro  Thr  Ile  Thr  Cys  Ser  Ser  Cys  Ser  Ser
               125                      130                          135

CAC  ATC  AAC  AGT  GTC  CAC  GTG  CAC  ATC  TCA  AAG  AGC  AAA  GTC  GGG  TGG          582
His  Ile  Asn  Ser  Val  His  Val  His  Ile  Ser  Lys  Ser  Lys  Val  Gly  Trp
               140                      145                     150
```

-continued

| Codon | Codon | Codon | Codon | Codon | Codon | Codon | Codon | Codon | Codon | Codon | Codon | Codon | Codon | Codon | Codon | Pos |
|---|---|---|---|---|---|---|---|---|---|---|---|---|---|---|---|---|
| CTG | ATC | CAA | CTC | TTC | CAC | AAA | AAA | ATT | GAG | TCT | GCG | CTT | CGA | AAC | AAG | 630 |
| Leu | Ile | Gln | Leu | Phe | His | Lys | Lys | Ile | Glu | Ser | Ala | Leu | Arg | Asn | Lys | |
| 155 | | | | | 160 | | | | | 165 | | | | | | |
| ATG | AAC | AGC | CAG | GTC | TGC | GAG | AAA | GTG | ACC | AAT | TCT | GTA | TCC | TCC | AAG | 678 |
| Met | Asn | Ser | Gln | Val | Cys | Glu | Lys | Val | Thr | Asn | Ser | Val | Ser | Ser | Lys | |
| 170 | | | | 175 | | | | | 180 | | | | | | 185 | |
| CTG | CAA | CCT | TAT | TTC | CAG | ACT | CTG | CCA | GTA | ATG | ACC | AAA | ATA | GAT | TCT | 726 |
| Leu | Gln | Pro | Tyr | Phe | Gln | Thr | Leu | Pro | Val | Met | Thr | Lys | Ile | Asp | Ser | |
| | | | | 190 | | | | | 195 | | | | | 200 | | |
| GTG | GCT | GGA | ATC | AAC | TAT | GGT | CTG | GTG | GCA | CCT | CCA | GCA | ACC | ACG | GCT | 774 |
| Val | Ala | Gly | Ile | Asn | Tyr | Gly | Leu | Val | Ala | Pro | Pro | Ala | Thr | Thr | Ala | |
| | | | 205 | | | | | 210 | | | | | 215 | | | |
| GAG | ACC | CTG | GAT | GTA | CAG | ATG | AAG | GGG | GAG | TTT | TAC | AGT | GAG | AAC | CAC | 822 |
| Glu | Thr | Leu | Asp | Val | Gln | Met | Lys | Gly | Glu | Phe | Tyr | Ser | Glu | Asn | His | |
| | | 220 | | | | | 225 | | | | | 230 | | | | |
| CAC | AAT | CCA | CCT | CCC | TTT | GCT | CCA | CCA | GTG | ATG | GAG | TTT | CCC | GCT | GCC | 870 |
| His | Asn | Pro | Pro | Pro | Phe | Ala | Pro | Pro | Val | Met | Glu | Phe | Pro | Ala | Ala | |
| | 235 | | | | | 240 | | | | | 245 | | | | | |
| CAT | GAC | CGC | ATG | GTA | TAC | CTG | GGC | CTC | TCA | GAC | TAC | TTC | TTC | AAC | ACA | 918 |
| His | Asp | Arg | Met | Val | Tyr | Leu | Gly | Leu | Ser | Asp | Tyr | Phe | Phe | Asn | Thr | |
| 250 | | | | | 255 | | | | | 260 | | | | | 265 | |
| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr | Gln | Glu | Ala | Gly | Val | Leu | Lys | Met | Thr | Leu | Arg | |
| | | | | 270 | | | | | 275 | | | | | 280 | | |
| GAT | GAC | ATG | ATT | CCA | AAG | GAG | TCC | AAA | TTT | CGA | CTG | ACA | ACC | AAG | TTC | 1014 |
| Asp | Asp | Met | Ile | Pro | Lys | Glu | Ser | Lys | Phe | Arg | Leu | Thr | Thr | Lys | Phe | |
| | | | 285 | | | | | 290 | | | | | 295 | | | |
| TTT | GGA | ACC | TTC | CTA | CCT | GAG | GTG | GCC | AAG | AAG | TTT | CCC | AAC | ATG | AAG | 1062 |
| Phe | Gly | Thr | Phe | Leu | Pro | Glu | Val | Ala | Lys | Lys | Phe | Pro | Asn | Met | Lys | |
| | | | 300 | | | | | 305 | | | | | 310 | | | |
| ATA | CAG | ATC | CAT | GTC | TCA | GCC | TCC | ACC | CCG | CCA | CAC | CTG | TCT | GTG | CAG | 1110 |
| Ile | Gln | Ile | His | Val | Ser | Ala | Ser | Thr | Pro | Pro | His | Leu | Ser | Val | Gln | |
| | 315 | | | | | 320 | | | | | 325 | | | | | |
| CCC | ACC | GGC | CTT | ACC | TTC | TAC | CCT | GCC | GTG | GAT | GTC | CAG | GCC | TTT | GCC | 1158 |
| Pro | Thr | Gly | Leu | Thr | Phe | Tyr | Pro | Ala | Val | Asp | Val | Gln | Ala | Phe | Ala | |
| 330 | | | | | 335 | | | | | 340 | | | | | 345 | |
| GTC | CTC | CCC | AAC | TCC | TCC | CTG | GCT | TCC | CTC | TTC | CTG | ATT | GGC | ATG | CAC | 1206 |
| Val | Leu | Pro | Asn | Ser | Ser | Leu | Ala | Ser | Leu | Phe | Leu | Ile | Gly | Met | His | |
| | | | | 350 | | | | | 355 | | | | | 360 | | |
| ACA | ACT | GGT | TCC | ATG | GAG | GTC | AGC | GCC | GAG | TCC | AAC | AGG | CTT | GTT | GGA | 1254 |
| Thr | Thr | Gly | Ser | Met | Glu | Val | Ser | Ala | Glu | Ser | Asn | Arg | Leu | Val | Gly | |
| | | | 365 | | | | | 370 | | | | | 375 | | | |
| GAG | CTC | AAG | CTG | GAT | AGG | CTG | CTC | CTG | GAA | CTG | AAG | CAC | TCA | AAT | ATT | 1302 |
| Glu | Leu | Lys | Leu | Asp | Arg | Leu | Leu | Leu | Glu | Leu | Lys | His | Ser | Asn | Ile | |
| | | 380 | | | | | 385 | | | | | 390 | | | | |
| GGC | CCC | TTC | CCG | GTT | GAA | TTG | CTG | CAG | GAT | ATC | ATG | AAC | TAC | ATT | GTA | 1350 |
| Gly | Pro | Phe | Pro | Val | Glu | Leu | Leu | Gln | Asp | Ile | Met | Asn | Tyr | Ile | Val | |
| | 395 | | | | | 400 | | | | | 405 | | | | | |
| CCC | ATT | CTT | GTG | CTG | CCC | AGG | GTT | AAC | GAG | AAA | CTA | CAG | AAA | GGC | TTC | 1398 |
| Pro | Ile | Leu | Val | Leu | Pro | Arg | Val | Asn | Glu | Lys | Leu | Gln | Lys | Gly | Phe | |
| 410 | | | | | 415 | | | | | 420 | | | | | 425 | |
| CCT | CTC | CCG | ACG | CCG | GCC | AGA | GTC | CAG | CTC | TAC | AAC | GTA | GTG | CTT | CAG | 1446 |
| Pro | Leu | Pro | Thr | Pro | Ala | Arg | Val | Gln | Leu | Tyr | Asn | Val | Val | Leu | Gln | |
| | | | | 430 | | | | | 435 | | | | | 440 | | |
| CCT | CAC | CAG | AAC | TTC | CTG | CTG | TTC | GGT | GCA | GAC | GTT | GTC | TAT | AAA | | 1491 |
| Pro | His | Gln | Asn | Phe | Leu | Leu | Phe | Gly | Ala | Asp | Val | Val | Tyr | Lys | | |
| | | 445 | | | | | 450 | | | | | 455 | | | | |

```
TGAAGGCACC AGGGGTGCCG GGGGCTGTCA GCCGCACCTG TTCCTGATGG GCTGTGGGGC    1551

ACCGGCTGCC TTTCCCCAGG GAATCCTCTC CAGATCTTAA CCAAGAGCCC CTTGCAAACT    1611
```

```
TCTTCGACTC AGATTCAGAA ATGATCTAAA CACGAGGAAA CATTATTCAT TGGAAAAGTG    1671

CATGGTGTGT ATTTTAGGGA TTATGAGCTT CTTTCAAGGG CTAAGGCTGC AGAGATATTT    1731

CCTCCAGGAA TCGTGTTTCA ATTGTAACCA AGAAATTTCC ATTTGTGCTT CATGAAAAAA    1791

AACTTCTGGT TTTTTTCATG TG                                             1813
```

(2) INFORMATION FOR SEQ ID NO:2:

(i) SEQUENCE CHARACTERISTICS:
  (A) LENGTH: 487 amino acids
  (B) TYPE: amino acid
  (D) TOPOLOGY: linear (ii) MOLECULE TYPE: protein (xi) SEQUENCE DESCRIPTION: SEQ ID NO:2:

```
Met Arg Glu Asn Met Ala Arg Gly Pro Cys Asn Ala Pro Arg Trp Val
-31 -30             -25                 -20
Ser Leu Met Val Leu Val Ala Ile Gly Thr Ala Val Thr Ala Ala Val
-15             -10                  -5                        1
Asn Pro Gly Val Val Val Arg Ile Ser Gln Lys Gly Leu Asp Tyr Ala
             5                  10                  15
Ser Gln Gln Gly Thr Ala Ala Leu Gln Lys Glu Leu Lys Arg Ile Lys
            20                  25                  30
Ile Pro Asp Tyr Ser Asp Ser Phe Lys Ile Lys His Leu Gly Lys Gly
        35                  40                  45
His Tyr Ser Phe Tyr Ser Met Asp Ile Arg Glu Phe Gln Leu Pro Ser
 50                 55                  60                    65
Ser Gln Ile Ser Met Val Pro Asn Val Gly Leu Lys Phe Ser Ile Ser
                70                  75                  80
Asn Ala Asn Ile Lys Ile Ser Gly Lys Trp Lys Ala Gln Lys Arg Phe
             85                  90                  95
Leu Lys Met Ser Gly Asn Phe Asp Leu Ser Ile Glu Gly Met Ser Ile
            100                 105                 110
Ser Ala Asp Leu Lys Leu Gly Ser Asn Pro Thr Ser Gly Lys Pro Thr
        115                 120                 125
Ile Thr Cys Ser Ser Cys Ser Ser His Ile Asn Ser Val His Val His
130                 135                 140                    145
Ile Ser Lys Ser Lys Val Gly Trp Leu Ile Gln Leu Phe His Lys Lys
                150                 155                 160
Ile Glu Ser Ala Leu Arg Asn Lys Met Asn Ser Gln Val Cys Glu Lys
            165                 170                 175
Val Thr Asn Ser Val Ser Ser Lys Leu Gln Pro Tyr Phe Gln Thr Leu
            180                 185                 190
Pro Val Met Thr Lys Ile Asp Ser Val Ala Gly Ile Asn Tyr Gly Leu
        195                 200                 205
Val Ala Pro Pro Ala Thr Thr Ala Glu Thr Leu Asp Val Gln Met Lys
210                 215                 220                    225
Gly Glu Phe Tyr Ser Glu Asn His His Asn Pro Pro Phe Ala Pro
                230                 235                 240
Pro Val Met Glu Phe Pro Ala Ala His Asp Arg Met Val Tyr Leu Gly
            245                 250                 255
Leu Ser Asp Tyr Phe Phe Asn Thr Ala Gly Leu Val Tyr Gln Glu Ala
        260                 265                 270
Gly Val Leu Lys Met Thr Leu Arg Asp Asp Met Ile Pro Lys Glu Ser
        275                 280                 285
```

|     |     |     |     |     |     |     |     |     |     |     |     |     |     |     |     |
|-----|-----|-----|-----|-----|-----|-----|-----|-----|-----|-----|-----|-----|-----|-----|-----|
| Lys 290 | Phe | Arg | Leu | Thr | Thr 295 | Lys | Phe | Phe | Gly | Thr 300 | Phe | Leu | Pro | Glu | Val 305 |
| Ala | Lys | Lys | Phe | Pro 310 | Asn | Met | Lys | Ile | Gln 315 | Ile | His | Val | Ser | Ala 320 | Ser |
| Thr | Pro | Pro | His 325 | Leu | Ser | Val | Gln | Pro 330 | Thr | Gly | Leu | Thr | Phe 335 | Tyr | Pro |
| Ala | Val | Asp 340 | Val | Gln | Ala | Phe | Ala 345 | Val | Leu | Pro | Asn | Ser 350 | Ser | Leu | Ala |
| Ser | Leu 355 | Phe | Leu | Ile | Gly | Met 360 | His | Thr | Thr | Gly | Ser 365 | Met | Glu | Val | Ser |
| Ala 370 | Glu | Ser | Asn | Arg | Leu 375 | Val | Gly | Glu | Leu | Lys 380 | Leu | Asp | Arg | Leu | Leu 385 |
| Leu | Glu | Leu | Lys | His 390 | Ser | Asn | Ile | Gly | Pro 395 | Phe | Pro | Val | Glu | Leu 400 | Leu |
| Gln | Asp | Ile | Met 405 | Asn | Tyr | Ile | Val | Pro 410 | Ile | Leu | Val | Leu | Pro 415 | Arg | Val |
| Asn | Glu | Lys 420 | Leu | Gln | Lys | Gly | Phe 425 | Pro | Leu | Pro | Thr | Pro 430 | Ala | Arg | Val |
| Gln | Leu 435 | Tyr | Asn | Val | Val | Leu 440 | Gln | Pro | His | Gln | Asn 445 | Phe | Leu | Leu | Phe |
| Gly 450 | Ala | Asp | Val | Val | Tyr 455 | Lys |     |     |     |     |     |     |     |     |     |

ANTI-CHLAMYDIAL USES OF BPI PROTEIN PRODUCTS

BACKGROUND OF THE INVENTION

The present invention relates generally to methods of treating chlamydial infections by administration of bactericidal/permeability-increasing (BPI) protein products.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. amino acid sequence is set out in SEQ ID NO: 1 hereto.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., *J. Bio. Chem.*, 262:14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. Gazzano-Santoro et al., *Infect. Immun.* 60:4754–4761 (1992).

The bactericidal effect of BPI has been reported to be highly specific to gram-negative species, e.g., in Elsbach and Weiss, *Inflammation: Basic Principles and Clinical Correlates*, eds. Gallin et al., Chapter 30, Raven Press, Ltd. (1992). This reported target cell specificity was believed to be the result of the strong attraction of BPI for lipopolysaccharide (LPS), which is unique to the outer membrane (or envelope) of gram-negative organisms. Although BPI was commonly thought to be non-toxic for other microorganisms, including yeast, and for higher eukaryotic cells, it has recently been discovered that BPI protein products, as defined infra, exhibit activity against gram-positive bacteria, mycoplasma, mycobacteria, fungi, and protozoa. [See allowed, co-owned, co-pending U.S. patent application Ser. No. 08/372,783 filed Jan. 13, 1995, the disclosures of which are incorporated herein by reference; co-owned, co-pending U.S. patent application Ser. No. 08/626,646, the disclosures of which are incorporated herein by reference; co-owned, co-pending U.S. patent application Ser. No. 08/372,105, the disclosures of which are incorporated herein by reference; and co-owned, co-pending U.S. patent application Ser. No. 08/273,470, the disclosures of which are incorporated herein by reference.] It has also been discovered that BPI protein products have the ability to enhance the activity of antibiotics against bacteria. [See U.S. Pat. No. 5,523,288, the disclosures of which are incorporated herein by reference, and allowed, co-owned, co-pending U.S. patent application Ser. No. 08/372,783.]

The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et al., *J. Clin. Invest.*, 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to LPS leads to organizational changes that probably result from binding to the anionic groups of LPS, which normally stabilize the outer membrane through binding of $Mg^{++}$ and $Ca^{++}$. Attachment of BPI to the outer membrane of gram-negative bacteria produces rapid permeabilization of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms [Weiss et al., *J. Clin. Invest.* 65: 619–628 (1980)]. This first stage of BPI action, permeabilization of the gram-negative outer envelope, is reversible upon dissociation of the BPI, a process requiring high concentrations of divalent cations and synthesis of new [LPS Weiss et al., *J. Immunol.* 132:3109–3115 (1984)]. Loss of gram-negative bacterial viability, however, is not reversed by processes which restore the envelope integrity, suggesting that the bactericidal action is mediated by additional lesions induced in the target organism and which may be situated at the cytoplasmic membrane (Mannion et al., *J. Clin. Invest.* 86: 631–641 (1990)). Specific investigation of this possibility has shown that on a molar basis BPI is at least as inhibitory of cytoplasmic membrane vesicle function as polymyxin B (In't Veld et al., *Infection and Immunity* 56:1203–1208 (1988)) but the exact mechanism as well as the relevance of such vesicles to studies of intact organisms has not yet been elucidated.

Chlamydia are nonmotile, gram-negative, obligate intracellular bacteria that have unusual biological properties which phylogenetically distinguish them from other families of bacteria. Chlamydiae are presently placed in their own order, the Chlamydiales, family Chlamydiaceae, with one genus, Chlamydia. [Schachter and Stamm, Chlamydia, in *Manual of Clinical Microbiology*, pages 669–677, American Society for Microbiology, Washington, D.C. (1995).] There are four species, *Chlamydia trachomatis, C. pneumoniae, C. psittaci* and *C. pecorum*, which cause a wide spectrum of human diseases. In developing countries, *C. trachomatis* causes trachoma, the world's leading cause of preventable blindness. Over 150 million children have active trachoma, and over 6 million people are currently blind from this disease. In industrialized countries, *C. trachomatis* is the most prevalent sexually transmitted disease, causing urethritis, cervicitis, epididymitis, ectopic pregnancy and pelvic inflammatory disease. Last year alone, an estimated 300 million people contracted sexually transmitted chiamydial infections. Among the 250,000 cases of pelvic inflammatory disease per year in the United States, approximately 25,000 women are rendered infertile each year. Neonatal *C. trachomatis* infections, contracted at birth from infected mothers, cause hundreds of thousands of conjunctivitis cases per year, of which about half of these infected infants develop pneumonia. Recently, *C. pneumoniae* has been implicated as a common cause of epidemic human pneumonitis. Members of the genus are not only important human pathogens, but also cause significant morbidity in other mammals and birds. Thus, chlamydia are one of the most ubiquitous pathogens in the animal kingdom. [Zhang et al., *Cell*, 69:861–869 (1992).]

Their unique developmental cycle differentiates them from all other microorganisms. They are obligate intracellular parasites that are unable to synthesize ATP, and thus depend on the host cells' energy to survive. Unlike viruses, they always contain both DNA and RNA, divide by binary fission, contain ribosomes, and can synthesize proteins. Chlamydia have cell walls similar in structure to those of gram-negative bacteria, and all members of the genus carry a unique LPS-like antigen, termed complement fixation (CF) antigen, that may be analogous to the LPS of certain gram-negative bacteria. [Schachter and Stamm, supra.] Chlamydia also carry a major outer membrane protein (MOMP) that contains both species and subspecies-specific antigens.

The infectious form of chlamydia is the elementary body (EB), which infects mammalian cells by attaching to the host cell and entering in a host-derived phagocytic vesicle (endosome), within which the entire growth cycle is completed. The target host cell in vivo is typically the columnar epithelial cell, and the primary mode of entry is believed to be recept-ormediated endocytosis. Once the EB has entered the cell, it reorganizes into a reticulate body (RB) that is larger than the EB and metabolically active, synthesizing DNA, RNA and proteins. The EBs are specifically adapted for extracellular survival, while the metabolically active RBs do not survive well outside the host cell and seems adapted for an intracellular milieu. After approximately 8 hours, the RBs begin dividing by binary fission. As they replicate within the endosomes of host cells, they form characteristic intracellular inclusions that can be seen by light microscopy. After a period of growth and division, the RBs reorganize and condense to form infectious EBs. The developmental cycle is complete when host cell lysis or exocytosis of chlamydia occurs, releasing the EBs to initiate another cycle of infection. The length of the complete developmental cycle, as studied in cell culture models, is 48 to 72 hours and varies as a function of the infecting strain, host cell and environmental conditions. [Beatty et al., *Microbiol. Rev.*, 58(4):686–699 (1994).]

It has been demonstrated, at least for *C. trachomatis*, that attachment of the chlamydia organism to host cells is mediated by a heparan sulfate-like glycosaminoglycan (GAG) present on the surface of the chlamydia. Treatment of chlamydia with either purified heparin, heparin sulfate, or heparin receptor analogs (such as platelet factor 4 and fibronectin, both of which are known to bind heparin sulfate), inhibited the attachment and infectivity of chlamydia to host cells. Inhibition was not seen with non-heparin GAGs, such as hyaluronate, chondroitin sulfate, or keratin sulfate. Treatment of *C. trachomatis* with heparitinase reduced attachment and infectivity by greater than 90%; subsequent treatment with exogenous heparan sulfate was able to restore the ability of treated organisms to attach to host cells in a dose-dependent manner. Other GAGs such as hyaluronate, chondroitin sulfate, or keratin sulfate did not restore attachment ability. These data suggest that a heparin sulfate-like GAG mediates attachment of chlamydia to host cells by bridging mutual GAG receptors on the host cell surface and on the chlamydial outer membrane surface. [Zhang et al., *Cell*, 69:861–869 (1992).]

*C. trachomatis* is almost exclusively a human pathogen and is responsible for trachoma, inclusion conjunctivitis, lymphogranuloma venereum (LGV), and genital tract diseases. [Schachter and Stamm, supra.] Within this species, serotypes A, B, Ba, and C have been associated with endemic trachoma, the most common preventable form of blindness in the world. Trachoma is a chronic inflammation of the conjunctiva and the cornea, which is not sexually transmitted. The potentially blinding sequelae of trachoma include lid distortion, trichiasis (misdirection of lashes), and entropion (inward deformation of the lid margin). These can cause corneal ulceration followed by loss of vision. Serotypes L1, L2, and L3 of *C. trachomatis* are associated with LGV. Untreated, lymphogranuloma venereum progresses through three stages, each more severe than the preceding one. The primary lesion, if present, appears on the genitals. The second stage is a bubonic state marked by regional lymphadenopathy, during which the buboes may suppurate and develop draining fistulas. Rectal strictures and lymphatic obstruction can appear in the tertiary stage. Lymphogranuloma venereum is a common problem in developing countries with tropical or subtropical climates, especially among the lower socioeconomic groups.

*C. trachomatis* is also the most common agent of sexually transmitted disease. In men, serotypes D through K are the major identifiable causes of nongonococcal urethritis, and also cause epididymitis, Reiter's syndrome, and proctitis. Chlamydial infections are not easily identified in men by clinical symptoms alone, because the infection may be asymptomatic and because other pathogens cause similar symptoms. Chlamydial urethritis occurs twice as frequently as gonococcal urethritis (gonorrhea) in some populations, and its incidence is on the increase. Even when *N. gonorrhea* is shown to be present, the urethritis may be due to a dual or multiple infection involving a second organism. Concurrent *C. trachomatis* and *N. gonorrhoea* infections have been reported in about 25 percent of men with gonorrhea. Epididymitis is the most important complication of chlamydial urethritis in men. *C. trachomatis* causes one of every two cases of epididymitis in younger men in the United States, with sterility a possible result. Reiter's syndrome is another manifestation of chlamydial infection in men. It is a painful systemic illness that classically includes symptoms of urethritis, conjunctivitis and arthritis. Urethritis and arthritis are by far the most frequent combination; it appears that the chlamydial urethral infection may trigger the arthritis. *C.*

*trachomatis* can also cause proctitis (anal inflammation), particularly in homosexual men.

In women, chlamydial infecton with the sexually transmitted serotypes results in cervicitis, urethritis, endometritis, salpingitis, and proctitis; serious sequelae of salpingitis include tubal scarring, infertility, and ectopic pregnancy. Unrecognized chlamydial infections in women are common. Approximately 50 percent of women infected with chlamydia are asymptomatic. *C. trachomatis* causes mucopurulent cervicitis and the urethral syndrome, as well as endometritis and salpingitis. These upper genital tract chlamydial infections may cause sterility or predispose to ectopic pregnancies and are the gravest complications of chlamydial infections in women. Ten percent of all maternal deaths are due to ectopic pregnancies. *C. trachomatis* causes over 30 percent of the cases of mucopurulent cervicitis. As many as one-half of the women with gonococcal cervicitis have a concomitant chlamydial infection. If the gonococcal infection is treated with penicillin, the concomitant chlamydial cervicitis will continue undetected and untreated, and may progress to pelvic inflammatory disease (salpingitis), which can lead to sterility and ectopic pregnancies. *C. trachomatis* is a cause of the urethral syndrome in women. Chlamydial infections may ascend from the cervix to the endometrium, where *C. trachomatis* has been found in the epithelial lining of the uterine cavity. It is estimated that about one-half of all women will cervicitis have endometritis. Salpingitis. a major cause of ectopic pregnancies and infertility, is the most serious complication of female genital infections. Upper abdominal pain is the predominant symptom of perihepatitis. Both *C. trachonatis* and *N. gonorrhoea* can cause perihepatitis. This condition occurs almost exclusively in women in whom the infecting organisms spread to the surface of the liver from inflamed fallopian tubes.

Women infected with *C. trachomatis* may also pass the disease to their newborn as it passes through the infected birth canal. These newborns most often develop inclusion conjunctivitis or chlamydial pneumonia, but may also develop vaginal, pharyngeal, or enteric infections. Though not blinding, inclusion conjunctivitis can become chronic, causing mild scarring and pannus formulation if left untreated. During passage through the birth canal, up to two-thirds of babies born to mothers with chlamydial genital infections will also become infected. With as many as one in ten pregnant women having chlamydial cervicitis in some parts of the world, the risk to newborns is considerable. Chlamydial pneumonia occurs in 10 percent to 20 percent of infants born to infected mothers. *C. trachomatis* is responsible for 20 percent to 60 percent of all pneumonias during the first 6 months of life.

*C. trachomatis* strains are sensitive to the action of tetracyclines, macrolides and sulfonamides and produce a glycogen-like material within the inclusion vacuole that stains with iodine.

*C. psittaci* strains infect many avian species and mammals, producing such diseases as psittacosis, ornithosis, feline pneumonitis, and bovine abortion. [Schachter and Stamm, supra.] *C. psittaci* is ubiquitous among avian species, and infection in birds usually involves the intestinal tract. The organism is shed in the feces, contaminates the environment, and is spread by aerosol. *C. psittaci* is also common in domestic mammals. In some parts of the world, these infections have important economic consequences, as *C. psittaci* is a cause of a number of systemic and debilitating diseases in domestic mammals and, most important, can cause abortions. Human chlamydial infections from this agent usually result from exposure to an infected avian species, but may also occur after exposure to infected domestic mammals. This species is resistant to the action of sulfonamides and produces inclusions that do not stain with iodine.

*C. pneumoniae* has less than 10% DNA relatedness to the other species and has pear-shaped rather than round elementary bodies (EBs). Like *C. trachomatis*, it appears to be exclusively a human pathogen without an animal reservoir. *C. pneumoniae* has been identified as the cause of a variety of respiratory tract diseases and is distributed worldwide. [Schachter and Stamm, supra.] Infections appear to be commonly acquired in later childhood, adolescence, and early adulthood, resulting in seroprevalences of 40 to 50% in 30 to 40-year-old people. Manifestations of infection include pharyngitis, bronchitis, and mild pneumonia, and transmission is primarily via respiratory secretions. In seroepidemiological studies, these infections have been linked with coronary artery disease, and their role in atherosclerosis is currently under intense scrutiny.

The role of *C. pecorum* as a pathogen is not clear, and specialized reagents are required for its identification.

The recommended procedure for primary isolation of chlamydia is cell culture. Chlamydia will grow in the yolk sac of the embryonated hen egg, as well as in cell culture (with some variability). *C. trachomatis* can infect several cell lines, such as McCoy's heteroploid murine cells, HeLa 229 cells, BHK-21 cells, or L-929 cells. HL cells and Hep-2 cells may be more sensitive for the recovery of *C. pneumoniae*. The most common technique involves inoculation of clinical specimens into cycloheximide-treated McCoy cells. The basic principle involves centrifugation of the inoculum onto the cell monolayer, incubation of the monolayers for 48 to 72 hours, and demonstration of typical intracytoplasmic inclusions by appropriate immunofluorescence, iodine or Giemsa staining procedures. Cell culture generally requires two to six days to complete because of the incubation time required.

Chlamydia may also be detected in samples by the direct fluorescent antibody (DFA) test, in which slides are incubated with fluorescein-conjugated monoclonal antibodies, and fluorescing elementary bodies are detected using a fluorescent microscope. This test has approximately 80% to 90% sensitivity and 98% to 99% specificity compared with cell cultures when both tests are performed under ideal circumstances. [Schachter and Stamm, supra.]

A number of commercially available products can detect chlamydial antigens in clinical specimens by using enzyme immunoassay (EIA) procedures. Most of these products detect chlamydial LPS, which is more soluble than MOMP. Without confirmation, the tests have a specificity on the order of 97%. [Schachter and Stamm, supra.] Several nucleic acid probes are also commercially available. One commercially available probe test (GenProbe) utilizes DNA-RNA hybridization in an effort to increase sensitivity by detecting chlamydial RNA.

The complement fixation (CF) test is the most frequently performed serological test, and measures serum level of complement-fixing antibody (antibody to the group CF antigen). It is useful for diagnosing psittacosis, in which paired acute- and convalescent-phase sera often show fourfold or greater increases in titer. The same seems to be true for many *C. pneumoniae* infections. Approximately 50% of these infections are CF-positive, although it may take 24 weeks to detect seroconversion. CF testing may also be useful in diagnosing LGV, in which single-point titers greater than 1:64 are highly supportive of this clinical diagnosis. [Schachter and Stamm, supra.] High titers of complement-fing antibodies are not found in chlamydial conjunctivitis or genital tract infections, and therefore are not sensitive for these infections.

The microimmunofluorescence (micro-IF) method is a much more sensitive procedure for measuring anti-chlamydial antibodies. This indirect fluorescent antibody technique uses antigens prepared by infecting the yolk sacs of fertile chick embryos with each chlamydial serotype. Serial dilutions of patient serum are added to the prepared antigens, and the level of antibody in the blood sample is determined with the use of immunofluorescence. Trachoma, inclusion conjunctivitis, and genital tract infections may be diagnosed by the micro-IF technique if appropriately timed paired sera can be obtained, but the procedure is of limited clinical utility because diagnosis requires demonstration of a four-fold or greater change in antibody titer in paired specimens. and because patients with superficial genital infections such as urethritis may not have a change in titer. However, a high antibody titer in a single serum specimen from a patient with Reiter's syndrome and a high IgM titer in the serum of an infant with pneumonia are helpful in establishing a diagnosis.

Strain-to-strain variation in antimicrobial susceptibility profiles and newly acquired drug resistance are both very infrequent among chlamydia. Among the drugs most active in vitro against *C. trachomatis, C. pneumoniae*, and *C. psittaci* are the tetracyclines, such as tetracycline and doxycycline, the macrolides, such as erythromycin and azithromycin, the quinolones, such as ciprofloxacin and ofloxacin, chloramphenicol, rifampin, clindamycin and the sulfonamides. The tetracyclines and macrolides have generally been the mainstays of therapy for infections due to chlamydia. [Schachter and Stamm, supra; Goodman and Gilman, *The Pharmacological Basis of Therapeutics*, 9th ed., McGraw-Hill, New York, N.Y. (1996).]

Antimicrobial susceptibility testing is infrequently performed for chlamydial infections, but may be conducted as follows. The organisms for testing are grown for at least two passages in cells cultured in antibiotic-free media before being harvested. An adjusted inoculum of ~100 inclusion-forming units per microtiter well is then used to infect antibiotic-free cell monolayers. After centrifugation of the inoculum onto the monolayer, serial dilutions of the test antibiotic can be added either immediately or at various time intervals over the next 24 hours. After 48 hours, fluorescein-conjugated monoclonal antibodies are use to identify minimum inhibitory concentration (MIC), i.e., the highest antibiotic dilution that inhibits intracellular inclusion formation. Generally, monolayers are also disrupted and further passaged to define the minimum bactericidal concentration (MBC), i.e., the highest antibiotic dilution that prevents viable chlamydia from being detected in passage (MBC).

SUMMARY OF THE INVENTION

The present invention provides methods of treating a subject suffering from a chlamydial infection by administering a therapeutically effective amount of a BPI protein product. This is based on the surprising discoveries that BPI protein products inhibit the infectivity of chlamydia and inhibit the proliferation of chlamydia in an established intracellular infection. The BPI protein products may be administered alone or in conjunction with other known anti-chlamydial agents. When made the subject of adjunctive therapy, the administration of BPI protein products may reduce the amount of non-BPI anti-chlamydial agent needed for effective therapy, thus limiting potential toxic response and/or high cost of treatment. Administration of BPI protein products may also enhance the effect of such agents, accelerate the effect of such agents, or reverse resistance of chlamydia to such agents.

In addition, the invention provides a method of killing or inhibiting growth of chlamydia comprising contacting the chlamydia with a BPI protein product. This method can be practiced in vivo or in a variety of in vitro uses such as use to decontaminate fluids and surfaces and to sterilize surgical and other medical equipment and implantable devices, including prosthetic joints and indwelling invasive devices.

A further aspect of the invention involves use of a BPI protein product for the manufacture of a medicament for treatment of chlamydial infection. The medicament may include, in addition to a BPI protein product, other chemotherapeutic agents such as non-BPI anti-chlamydial agents.

Numerous additional aspects and advantages of the invention will become apparent to those skilled in the art upon considering the following detailed description of the invention, which describes the presently preferred embodiments thereof.

DETAILED DESCRIPTION OF THE INVENTION

The present invention relates to the surprising discovery that a BPI protein product can be administered to treat subjects suffering from chlamydial infection, and provides methods of prophylactically or therapeutically treating such infections. Unexpectedly, BPI protein products were demonstrated to have anti-chlamydial activities, as measured, for example, by a reduction in the number of reproductive bodies seen in the host cells. A variety of chlamydial infections, including infections caused by *C. trachomatis, C. pneumoniae, C. psittaci* and *C. pecorum*, may be treated according to the invention.

The term "treating" or "treatment" as used herein encompasses both prophylactic and therapeutic treatment.

The BPI protein product may be administered systemically or topically. Systemic routes of administration include oral, intravenous, intramuscular or subcutaneous injection (including into depots for long-term release), intraocular or retrobulbar, intrathecal, intraperitoneal (e.g. by intraperitoneal lavage), transpulmonary using aerosolized or nebulized drug, or transdermal. Topical routes include administration in the form of salves, creams, jellies, ophthalmic drops or opthalmic ointments, ear drops, suppositories, such as vaginal suppositories, or irrigation fluids (for, e.g., irrigation of wounds).

When given parenterally, BPI protein product compositions are generally injected in doses ranging from 1 µg/kg to 100 mg/kg per day, preferably at doses ranging from 0.1 mg/kg to 20 mg/kg per day, and more preferably at doses ranging from 1 to 20 mg/kg/day. The treatment may continue by continuous infusion or intermittent injection or infuision, or a combination thereof, at the same, reduced or increased dose per day for as long as determined by the treating physician. When given topically, BPI protein product compositions are generally applied in unit doses ranging from 1 µg/mL to 1 gm/mL, and preferably in doses ranging from 1 µg/mL to 100 mg/mL. Those skilled in the art can readily optimize effective dosages and monotherapeutic or concurrent administration regimens for BPI protein product and/or other anti-chlamydial agents, as determined by good medical practice and the clinical condition of the individual patient.

The BPI protein product may be administered in conjunction with other anti-chlamydial agents presently known to be effective. Preferred anti-chlamydial agents for this purpose include the tetracyclines, such as tetracycline and doxycycline, the macrolides, such as erythromycin and azithromycin, the quinolones, such as ciprofloxacin and ofloxacin, chloramphenicol, rifampin, clindamycin and the sulfonamides. Concurrent administration of BPI protein product with anti-chlamydial agents is expected to improve the therapeutic effectiveness of the anti-chlamydial agents. This may occur through reducing the concentration of anti-chlamydial agent required to eradicate or inhibit chlamydial growth, e.g., replication. Because the use of some agents is limited by their by stemic toxicity or prohibitive cost, lowering the concentration of anti-chlamydial agent required for therapeutic effectiveness reduces toxicity and/or cost of treatment, and thus allows wider use of the agent. Concurrent administration of BPI protein product and another anti-chlamydial agent may produce a more rapid or complete bactericidal or bacteriostatic effect than could be achieved with either agent alone. BPI protein product administration may reverse the resistance of chlamydia to anti-chlamydial agents. BPI protein product administration may also convert a bacteriostatic agent into a bactericidal agent.

An advantage of the present invention is that the wide spectrum of activity of BPI protein products against a variety of organisms, and the use of BPI protein products as adjunctive therapy to enhance the activity of antibiotics makes BPI protein products an excellent choice for treating dual or multiple infections with chlamydia.and another organism, such as the gram-negative bacteria *N. gonorrhea*. Thus, BPI protein products may be especially useful in inhibiting transmission of sexually transmitted diseases, which often involve dual gonococcal/chlamydial infection. It is therefore contemplated that BPI protein products will be incorporated into contraceptive compositions and devices, e.g., included in spermicidal creams or jellies, or coated on the surface of condoms.

Another advantage is the ability to treat chlamydia that have acquired resistance to known anti-chlamydial agents. A further advantage of concurrent administration of BPI with an anti-chlamydial agent having undesirable side effects is the ability to reduce the amount of anti-chlamydial agent needed for effective therapy. The present invention may also provide quality of life benefits due to, e.g., decreased duration of therapy, reduced stay in intensive care units or reduced stay overall in the hospital, with the concomitant reduced risk of serious nosocomial (hospital-acquired) infections.

"Concurrent administration" as used herein includes administration of the agents together, or before or after each other. The BPI protein products and anti-chlamydial agents may be administered by different routes. For example, the BPI protein product may be administered intravenously while the anti-chlamydial agents are administered intramuscularly, intravenously, subcutaneously, orally or intraperitoneally. Alternatively, the BPI protein product may be administered intraperitoneally while the anti-chiamydial agents are administered intraperitoneally or intravenously, or the BPI protein product may be administered in an aerosolized or nebulized form while the anti-chiamydial agents are administered, e.g., intravenously. The BPI protein product and anti-chlamydial agents may be both administered intravenously. The BPI protein product and anti-chlamydial agents may be given sequentially in the same intravenous line, after an intermediate flush, or may be given in different intravenous lines. The BPI protein product and anti-chlamydial agents may be administered simultaneously or sequentially, as long as they are given in a manner sufficient to allow both agents to achieve effective concentrations at the site of infection.

Concurrent administration of BPI protein product and antibiotic is expected to provide more effective treatment of chlamydial infections. Concurrent administration of the two agents may provide greater therapeutic effects in vivo than either agent provides when administered singly. For example, concurrent administration may permit a reduction in the dosage of one or both agents with achievement of a similar therapeutic effect. Alternatively, the concurrent administration may produce a more rapid or complete bactericidal/bacteriostatic effect than could be achieved with either agent alone.

Therapeutic effectiveness is based on a successful clinical outcome, and does not require that the anti-chlamydial agent or agents kill 100% of the organisms involved in the infection. Success depends on achieving a level of anti-chlamydial activity at the site of infection that is sufficient to inhibit the chlamydia in a manner that tips the balance in favor of the host. When host defenses are maximally effective, the anti-chlamydial effect required may be minimal. Reducing organism load by even one log (a factor of 10) may permit the host's own defenses to control the infection. In addition, augmenting an early bactericidal/bacteriostatic effect can be more important than long-term bactericidal/bacteriostatic effect. These early events are a significant and critical part of therapeutic success, because they allow time for host defense mechanisms to activate.

BPI protein product is thought to interact with a variety of host defense elements present in whole blood or serum, including complement, p15 and LBP, and other cells and components of the immune system. Such interactions may result in potentiation of the activities of BPI protein product. Because of these interactions, BPI protein products can be expected to exert even greater activity in vivo than in vitro. Thus, while in vitro tests are predictive of in vivo utility, absence of activity in vitro does not necessarily indicate absence of activity in vivo. For example, BPI has been observed to display a greater bactericidal effect on gram-negative bacteria in whole blood or plasma assays than in assays using conventional media. [Weiss et al., *J. Clin. Invest.* 90:1122–1130 (1992)]. This may be because conventional in vitro systems lack the blood elements that facilitate or potentiate BPI's function in vivo, or because conventional media contain higher than physiological concentrations of magnesium and calcium, which are typically inhibitors of the activity of BPI protein products. Furthermore, in the host, BPI protein product is available to neutralize translocation of gram-negative bacteria and concomitant release of endotoxin, a further clinical benefit not seen in or predicted by in vitro tests.

It is also contemplated that the BPI protein product be administered with other products that potentiate the activity of BPI protein products, including the anti-chlamydial activity of BPI protein products. For example, serum complement potentiates the gram-negative bactericidal activity of BPI protein products; the combination of BPI protein product and serum complement provides synergistic bactericidal/growth inhibitory effects. See, e.g., Ooi et al. *J. Biol. Chem.*, 265: 15956 (1990) and Levy et al. *J. Biol. Chem.*, 268: 6038–6083 (1993) which address naturally-occurring 15 kD proteins potentiating BPI antibacterial activity. See also co-owned, co-pending PCT Application No. US94/07834 filed Jul. 13, 1994, which corresponds to U.S. patent application Ser. No. 08/274,303 filed Jul. 11, 1994 as a continuation-in-part of U.S. patent application Ser. No. 08/093,201 filed Jul. 14, 1993. These applications, which are all incorporated herein by reference, describe methods for potentiating gram-negative bactericidal activity of BPI protein products by administering lipopolysaccharide binding protein (LBP) and LBP protein products. LBP protein derivatives and derivative hybrids which lack CD-14 immunostimulatory properties are described in PCT Application No. US94/06931 filed Jun. 17, 1994, which corresponds to co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of all of which are hereby incorporated by reference. It has also been observed that poloxamer surfactants enhance the anti-bacterial activity of BPI protein products, as described in Lambert, U.S. application Ser. No. 08/586,133 filed Jan. 12, 1996, which is a continuation-in-part of U.S. application Ser. No. 08/530,599 filed Sep. 19, 1995, which is a continuation-in-part of U.S. application Ser. No. 08/372,104 filed Jan. 13, 1995, all of which correspond to PCT Application No. PCT/US96/01095; poloxamer surfactants may also enhance the activity of anti-chlamydial agents.

In addition, the invention provides a method of killing or inhibiting growth of chlamydia comprising contacting the chlamydia with a BPI protein product. This method can be practiced in vivo or in a variety of in vitro uses such as to decontaminate fluids and surfaces or to sterilize surgical and other medical equipment and implantable devices, including prostheses and intrauterine devices. These methods can also be used for in situ sterilization of indwelling invasive devices such as intravenous lines and catheters, which are often foci of infection.

A further aspect of the invention involves use of a BPI protein product for the manufacture of a medicament for treatment of chlamydial infection. The medicament may include, in addition to a BPI protein product, other chemotherapeutic agents such as anti-chlamydial agents. The medicament can optionally comprise a pharmaceutically acceptable diluent, adjuvant or carrier.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding, and methods for expression of, BPI proteins including recombinant BPI holoprotein, referred to as rBPI and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 to 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 145 and 146) set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in co-owned and co-pending U.S. patent application Ser. No. 08/112,132, filed Mar. 11, 1994, and corresponding PCT Application No. PCT/US95/03125, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064,693 filed May 19, 1993 and corresponding PCT Application No. US93/04754 filed May, 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A stable BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. co-owned and co-pending U.S. patent application Ser. No. 08/212,132 filed Mar. 11, 1994, and corresponding PCT Application No. PCT/US95/03125, the disclosures of which are incorporated herein by reference.

Other BPI protein products useful according to the methods of the invention are peptides derived from or based on BPI produced by recombinant or synthetic means (BPI-derived peptides), such as those described in co-owned and copending PCT Application No. US94/10427 filed Sep. 15, 1994, which corresponds to U.S. patent application Ser. No. 08/306,473, filed Sep. 15, 1994, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference.

Presently preferred BPI protein products include recombinantl-yproduced N-terminal fragments of BPI, especially those having a molecular weight of approximately between 21 to 25 kD such as $rBPI_{21}$ or $rBPI_{23}$, or dimeric forms of these N-terminal fragments (e.g., $rBPI_{42}$ dimer). Additionally, preferred BPI protein products include rBPI and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-chlamydial agents. A stable pharmaceutical composition containing BPI protein products (e.g., rBPI, $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (PLURONIC F-68, BASF Wyandotte, Parsippany, N.J.) and 0.002% by weight of polysorbate 80 (TWEEN 80, ICI Americas Inc., Wilmington, Del.). Another stable pharmaceutical composition containing BPI protein products (e.g., $rBPI_{21}$) comprises-the BPI protein product at a concentration of 2 mg/ml in 5 mM citrate, 150 mM NaCl, 0.2% poloxamer 188 and 0.002% polysorbate 80. Such preferred combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

The chemical formulas corresponding to the generic terminology poloxamer 188 and polysorbate 80 may be found in, e.g., CTFA *Cosmetic Ingredient Dictionary*, published by the Cosmetic, Toiletry and Fragrance Association, Washington, D.C. (1991).

Other aspects and advantages of the present invention will be understood upon consideration of the following illustrative examples. Example 1 addresses the use of BPI protein product to inhibit infection of host cells with chlamydia when administered at the same time as chlamydial challenge. Example 2 addresses the anti-chlamydial activity of BPI protein product in chlamydia-infected host cells.

EXAMPLE 1

Use of BPI Protein Product to Inhibit Infection of Host Cells with Chlamydia

A. Preparation of Chlamydia Stock

*Chlamydia trachomatis* (Ct) serovar L2 stock was prepared as follows. McCoy cells (ATCC Accession No. CRL 1696) were cultured overnight in growth medium [Eagles Medium Nutrient Mixture (MEM), M-3786, Sigma, St. Louis, Mo.] with 1% sodium pyruvate (S-8636, Sigma) and 10% fetal bovine serum (FBS, A115-L, Hyclone, Logan, Vt.). The media was aspirated and a vial of Ct was rapidly thawed and mixed with 30 mL of Dulbecco's phosphate buffered saline (PBS, Sigma) and 7% sucrose (DPBS-7). Ten mL of the suspension were added to each of 3 T150 flasks and the flasks were incubated at 37° C. while being rocked periodically over the next two hours to distribute the inoculum. The DPBS-7 was aspirated from the flasks and 50 mL of growth media were added to each flask. After incubation for three days at 37° C. in 5% $CO_2$, the Ct was harvested as follows. The growth media was aspirated from the flasks and glass beads were added to the flasks to a depth of ~0.25 inches. Ten mL Eagles MEM (without FBS) was added to each flask and the beads were rocked over the monolayer until all the cells were dislodged. The beads and cell debris were collected in 50 mL screw-capped centrifuge tubes, the flasks were washed twice with PBS, and the washings were added to the bead suspension. Each tube was placed on ice and sonicated for 60 seconds to disrupt the cells. The disrupted cells/bead suspension were centrifuged at low speed (~800 rpm). The supernatant was removed and collected in a 250 mL polycarbonate centrifuge bottle, then centrifuged for one hour at high speed (~25,000×g). The pellet was resuspended in FBS (40 mL) by repeated passage through a #16 gauge needle and syringe. One mL aliquots were distributed into NUNC® (Naperville, Ill.) cryovials and frozen at −70° C.

B. Titration of Chlamydia Stock

Three vials of Ct stock prepared as described above in Section A were rapidly thawed at 37° C. and serially diluted in 10-fold concentrations in Eagles MEM or DPBS-7 without serum. Twenty-four well plates with coverslips in each well containing 24-hour McCoy cell monolayers were prepared. The media was aspirated, the wells were washed once with PBS, and 1 mL of each Ct dilution in either Eagles MEM or DPBS-7 was added to quadruplicate sets of McCoy cells. The plates were incubated at 37° C. in 5% $CO_2$ for 2 hours, the media was aspirated, and 2 mL of growth media was added. The plates were then reincubated at 27° C. in 5% $CO_2$ for 3 days, fixed in methanol, and stained for 30 minutes in a moist chamber with an FITC-labelled mouse monoclonal anti-chlamydia antibody (Syva MicroTrak® Chlamydia trachomatis Culture Confirmation Test). The stained coverslips were washed in water, air dried, inverted into a drop of mounting fluid (50% glycerol; 50% PBS) and viewed using a Leitz fluorescent microscope with a 25× objective (excitation wavelength 480 nm. emission wavelength 520 nm). The inclusion bodies were counted and comparable results were obtained over the $10^{-2}$ to $10^{-10}$ concentration range tested in the Eagles MEM and DPBS-7. The $10^{-5}$ dilution of the stock preparation gave 100–300 inclusion body-forming units/mL; this dilution was selected for use in all subsequent studies using this Ct stock. Additional media studies were performed using Basal Medium Eagle (BME, Sigma), Eagles MEM (E-MEM, Sigma), RPMI-1640 with HEPES (Sigma), RPMI-1640 without HEPES (Sigma), F-12 (Gibco) and Dulbecco's Modified Eagle's Medium Nutrient Mixture F-12 Ham (DMEM/F-12, Gibco). DMEM/F-12 without FBS was selected for use in subsequent Chlamydia infectivity studies. Media without FBS was selected for use because the addition of 10% FBS to the above tested media inhibited infection of McCoy cells by Ct.

C. Infection by Chlamydia in the Presence or Absence of BPI Protein Product

The BPI protein product tested was $rBPI_{21}$ [2 mg/mL in 5 mM sodium citrate, 150 mM sodium chloride, pH 5.0, with 0.2% PLURONIC® P123 (BASF Wyandotte, Parsippany, N.J.), 0.002% polysorbate 80 (TWEEN® 80, ICI Americas Inc., Wilmington, Del.) and 0.05% EDTA]. Equal volumes of formulation buffer alone [5 mM sodium citrate, 150 mM sodium chloride, pH 5.0, with 0.2% PLURONIC® P123, 0.002% polysorbate 80 and 0.05% EDTA] were used as a control. Serial dilutions of $rBPI_{21}$ or formulation buffer were prepared with DMEM/F-12 (without FBS) so that when the serial dilutions were added at a 9:1 ratio to 1 mL of a $10^{-4}$ dilution of Ct stock, the final concentration of Ct would be a $10^{-5}$ dilution of Ct stock and the final $rBPI_{21}$ concentrations would be 128, 64, 32, 16 and 8 μg/mL. Comparable (by volume) formulation buffer controls were also prepared. The final suspensions were incubated at 37° C. for 30 minutes in a water bath.

McCoy cells in DMEM/F-12/10%FBS were seeded at $2 \times 10^5$ cells/well into 24-well tissue culture plates (Corning #25820), incubated for 24 hours and the media aspirated. Ct, with and without BPI, was added in 1 mL to duplicate wells at each $rBPI_{21}$ concentration. The plates were centrifuged at 2500 rpm for 30 minutes, incubated for 2 hours at 37° C. in 5% $CO_2$, and the wells aspirated. Each well received 2 mL of DMEM/F-12/10%FBS and 1 μg/mL cycloheximide (Sigma) and the plates reincubated for 3 days. After removal of the media, the wells were washed with phosphate buffered saline (PBS), air dried, fixed with methanol and stained with Gram's iodine. The cells may be alternatively stained with FITC-labelled anti-chlamydia antibodies as described in section B above.

Using an inverted microscope, 100% of each well was scanned for the presence of inclusion bodies, which stain brown with Gram's iodine due to the high concentration of glycogen in vacuoles produced by the reproductive bodies. Results are shown below in Table 1.

TABLE 1

| | Number of Inclusion Bodies per Well | |
|---|---|---|
| $rBPI_{21}$ Concentration | with $rBPI_{21}$ (mean of 4 wells) | without $rBPI_{21}$ (value for 1 well) |
| 128 μg/mL | 0 | 110 |
| 64 μg/mL | 0 | 115 |
| 32 μg/mL | 0 | 115 |
| 16 μg/mL | 1.5 | 114 |
| 8 μg/mL | 59 | 124 |
| Positive Control (Ct only) | | 151 |
| Negative Control (no Ct) | | 0 |

These representative results from one of three studies indicate that $rBPI_{21}$ can inhibit infection of permissive cells.

EXAMPLE 2

Anti-Chlamydial Activity of BPI Protein Product Against Chlamydia-Infected Host Cells

*Chlamydia trachomatis* (Ct) serovar L2 stock prepared as described in Example 1 was diluted to $10^{-5}$ with Dulbecco's Modified Eagle's Medium Nutrient Mixture F-12 Ham (DMEM/F-12) with 10% fetal bovine serum (FBS).

McCoy cells in DMEM/F-12/10%FBS were seeded at $1 \times 10^5$ cells/well into 24-well tissue culture plates (Corning #25820), incubated for 24 hours, and the media aspirated. Ct (1 mL of the $10^{-5}$ stock) was added to each well of four plates except for two negative control wells per plate. The plates were centrifuged at 2500 rpm for 30 minutes, incubated for 24 hours at 37° C. in 5% $CO_2$, and the wells aspirated.

$rBPI_{21}$ as described in Example 1 was diluted to final concentrations of 128, 64, 32, 16 and 8 μg/mL in DMEM/F-12 and 1.0 mL added to the appropriate duplicate wells on each plate. Comparable formulation buffer controls as described in Example 1 were also prepared. The plates were incubated for 2 hours, and 1 mL of DMEM/F-12/20%FBS and 2 μg/mL cycloheximide was added to all wells, causing the $rBPI_{21}$ concentration to decrease by a factor of two. The plates were reincubated for up to 5 days.

At 24, 48, 72 and 120 hours, the media was removed from a single plate, the wells washed with PBS and air dried, fixed with methanol and stained with Gram's iodine. Using an inverted microscope, 100% of each well was scanned for the presence of inclusion bodies. Results are shown in Table 2 below.

TABLE 2

| Initial $rBPI_{21}$ | Number of Inclusion Bodies Per Well | | |
|---|---|---|---|
| Concentration* | at 24 hours | at 48 hours | at 72 hours |
| 0 | 285.5 | 398 | 335.75 |
| 8 | 194.5 | 180 | 108 |
| 16 | 138 | 140.5 | 109.5 |
| 32 | 112.5 | 95 | 57.5 |
| 64 | 119.5 | 81 | 39 |
| 128 | 113 | 77.5 | 5 |

*This initial concentration, which was present for the first two hours of incubation, was decreased to half of the initial value for the remainder of the 5-day incubation.

These representative results from one of two studies show that $rBPI_{21}$ at initial concentrations ranging from 16 μg/mL to 128 μg/mL was able to reduce the number of intracellular inclusion, bodies in Ct-infected cells when administered 24 hours after challenge with Ct.

Numerous modifications and variations in the practice of the invention are expected to occur to those skilled in the art upon consideration of the foregoing description on the presently preferred embodiments thereof. Consequently the only limitations which should be placed upon the scope of the present invention are those that appear in the appended claims.

What is claimed are:

1. A method of treating chlamydial infections comprising administering to a subject suffering from a chlamydial infection a therapeutically effective amount of a bactericidal/permeability-increasing (BPI) protein product.

2. The method of claim 1 wherein the BPI protein product is BPI holoprotein, rBPI$_{23}$ or rBPI$_{21}$.

3. The method of claim 1 wherein the BPI protein product is administered at a dose of between 1 μg/kg to 100 mg/kg per day.

4. The method of claim 1 wherein the BPI protein product is administered topically at a unit dose of between 1 μg/mL to 1 gm/mL.

5. The method of claim 1 comprising the additional step of administering a non-BPI anti-chlamydial agent.

6. The method of claim 1 wherein the subject is suffering from coronary artery disease.

7. The method of claim 1 wherein the BPI protein product is an N-terminal fragment of BPI or dimeric form thereof.

8. The method of claim 7 wherein the N-terminal fragment has a molecular weight of about 21 kD to 25 kD.

9. The method of claim 1 wherein the subject is infected by a chlamydial species selected from the group consisting of *C. trachomatic, C. pneumoniae, C. psittaci* and *C. pecorum* species.

10. The method of claim 9 wherein the chlamydial species is *C. trachomatis*.

11. A method of killing or inhibiting replication of chlamydia comprising contacting the chlamydia with a bactericidal/permeability-increasing (BPI) protein product.

12. The method of claim 11 further comprising contacting the chlamydia with a non-BPI anti-chlamydial agent.

13. A method of killing or inhibiting replication of chlamydia in a subject suffering from coronary artery disease comprising contacting the chlamydia with a bactericidal/permeability-increasing protein product.

* * * * *

UNITED STATES PATENT AND TRADEMARK OFFICE
CERTIFICATE OF CORRECTION

PATENT NO. : 5,888,973
DATED : March 30, 1999
INVENTOR(S) : Lewis H. Lambert, Jr.

It is certified that error appears in the above-identified patent and that said Letters Patent is hereby corrected as shown below:

At col. 24, line 34, in claim 9,"*C. trachomatic*" should be --*C. trachomatis*--.

Signed and Sealed this

Tenth Day of October, 2000

Attest:

Q. TODD DICKINSON

*Attesting Officer*     *Director of Patents and Trademarks*